United States Patent [19]

Cooper

[11] Patent Number: 4,629,453
[45] Date of Patent: Dec. 16, 1986

[54] HYPODERMIC NEEDLE PROTECTION DEVICE

[76] Inventor: Tim M. Cooper, 1196 Kotenberg, San José, Calif. 95125

[21] Appl. No.: 766,713

[22] Filed: Aug. 19, 1985

[51] Int. Cl.$^4$ ............................................. A61M 5/32
[52] U.S. Cl. ..................................... 604/192; 604/263
[58] Field of Search ................. 604/192, 272, 263; 206/365

[56] References Cited

U.S. PATENT DOCUMENTS

| | | | |
|---|---|---|---|
| 3,021,942 | 2/1962 | Hamilton | 604/192 |
| 3,149,717 | 9/1964 | Castelli | 206/365 |
| 3,294,231 | 12/1966 | Vanderbeck | 206/365 |
| 3,434,473 | 3/1969 | Smith | 604/192 |

FOREIGN PATENT DOCUMENTS 265781 1/1966 Australia ............................ 206/365

OTHER PUBLICATIONS

Comp Gard TM brochure of Comp Equipment Corp.

Primary Examiner—John D. Yasko
Attorney, Agent, or Firm—Leonard Bloom

[57] ABSTRACT

A protective cap adapted to overly a hypodermic syringe needle and includes a radially extending flange extending beyond the outer periphery of the cap, which serves as a barrier should misalignment of the bore defining an interior of the cap and the needle occur. The cap is grasped on an end of the cap remote from the opening defining the bore so that the radially extending flange is interposed between the needle and the user's hand. A special cap storage receptacle is also provided.

4 Claims, 6 Drawing Figures

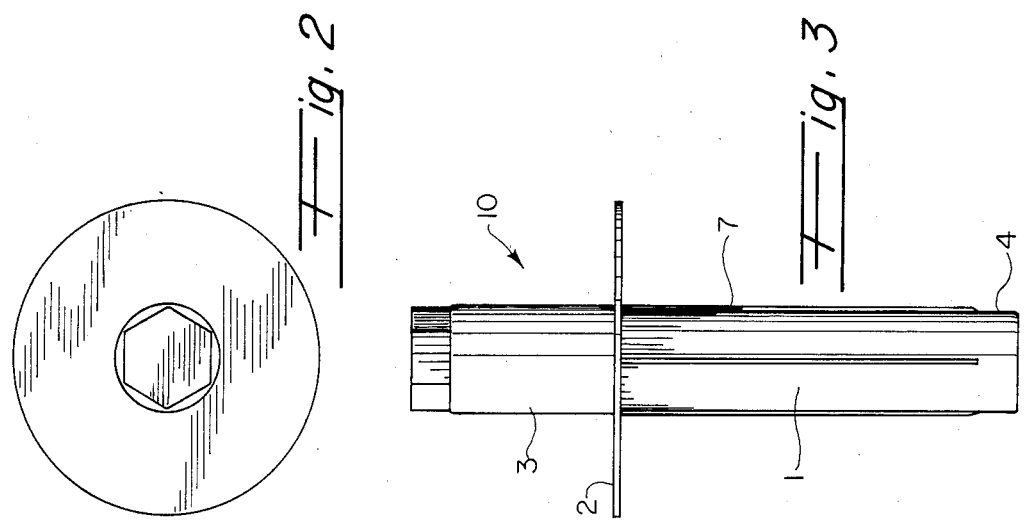
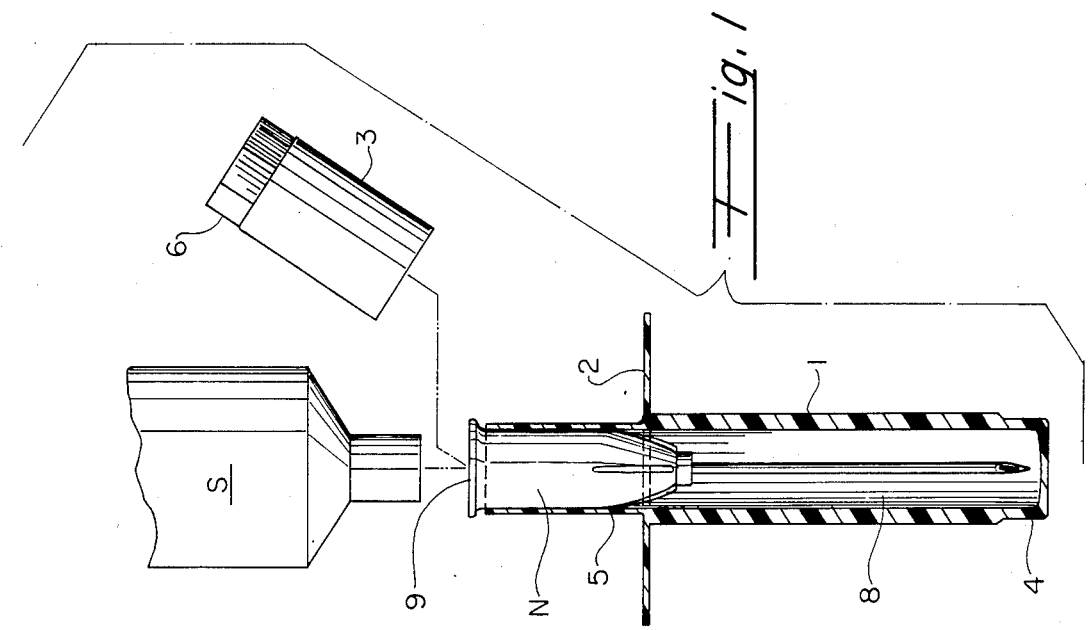

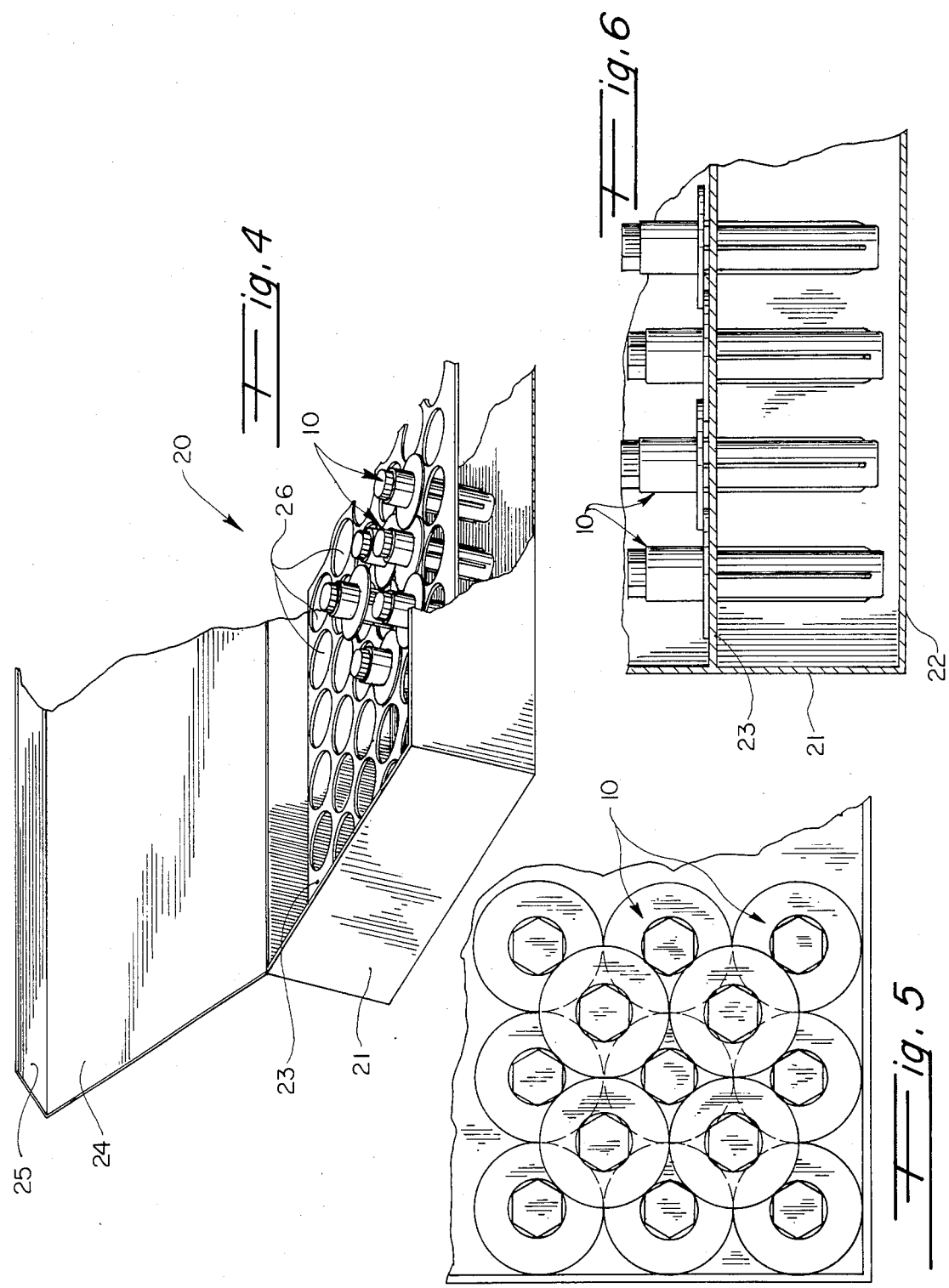

HYPODERMIC NEEDLE PROTECTION DEVICE

FIELD OF THE INVENTION

The field of the invention relates generally to protective caps adapted to be utilized with hypodermic needles for syringes.

BACKGROUND

It is well known that used hypodermic needles are extremely susceptible to transmitting diseases. Hepatitis and other highly contagious diseases can be transmitted by successive use of the same needle by different individuals. In a hospital environment, however, precautions are taken to avoid use of contaminated needles by their expeditious disposal. Problems exist, however, in storing the needle for disposal and commonly the protective cap associated with the needle receives the used needle for discarding. However, it is apparent that the bore of the needle cap is dimensioned not much larger than the diameter of the needle and its needle base which removably attaches to a syringe. Misalignment of the needle with respect to the cap when trying to reinsert the needle therein can cause the hand which holds the cap to be punctured thereby increasing the likelihood of transmission of a contagious disease.

The instant invention is directed to an instrumentality which renders it less likely that the holder of the cap will be contaminated by the needle when misalignment occurs. The needle receptacle, according to the present invention, includes a radially extending flange which is interposed between the hand grasping area and the opening of the receptacle so that, absent gross misalignment, it is more likely that the protective flange would be engaged by the needle rather than the person's hand when recapping the needle.

SUMMARY OF THE INVENTION

It is the primary object of the invention to provide the needle/syringe with a protective cap device having a radially extending (annular) flange that is easy and inexpensive to manufacture by being easily molded.

It is further the object of the invention to provide a device of the character above which reduces the likelihood of self inflicted injury by interposing a special protective flange between the combined syringe/needle and the hand-held hypodermic needle cap.

It is further the object of this invention to provide a device as characterized above which lends itself to mass productive techniques.

More particularly, these objects and other related objects will become evident when considering the following detailed specification when taken in conjunction with the appended drawing figures. Specifically, however, the instant invention is directed to an instrumentality adapted to overlie the needle portion of a syringe and frictionally engage the needle base where it attaches the syringe so that needles can be successively replaced. In order to cause the needle to be placed within the cap, alignment of the needle with the bore of the cap must be effected, and when misalignment occurs, the hand of the person holding the cap can be contaminated by inadvertent needle injection. Thus a radially extending flange is provided on the outer wall of the cap to locate the hand on one side of the flange remote from the opening of the blind bore of the cap. Thus misalignment between the needle and the bore will cause the needle to more likely engage the flange rather than the hand of the person holding the cap. The cap itself is provided with a closure which allows a needle to be stored within the cap free from contamination and available for use upon demand. A plurality of caps and closures are contained in a receptacle.

DESCRIPTION OF THE DRAWING FIGURES

FIG. 1 is a sectional view taken along a longitudinal axis of the apparatus according to the present invention.

FIG. 2 is a top plan view of that which is shown in FIG. 1.

FIG. 3 is a side view.

FIG. 4 is a perspective view of a plurality of protective caps stored in an associated special receptacle.

FIG. 5 is a top plan view thereof.

FIG. 6 is a partial sectional view showing the nested arrangement of a plurality of protective caps when placed in the receptacle in FIG. 4.

BRIEF DESCRIPTION OF THE DRAWINGS

Referring to the drawings wherein like reference number refers to like parts throughout the various drawing figures, reference numeral 10 is directed to the protective cap for use with hypodermic needles and syringes according to the present invention.

More particularly, the protective cap according to the present invention includes a tubular body 1 having an end wall 4, the tubular body combined with the end wall 4 defining an interior 8 having an opening 9 with the interior defining a blind bore.

The body 1 has a radially extending flange 2 spaced downwardly from opening 9 approximately one third the body's total length. FIG. 3 reflects that the body 1 below the flange has a plurality of longitudinally extending ribs 7 running down from the flange to the end wall 4. The ribs 7 provide a tractive surface to facilitate grasping the body for needle or cover manipulation.

FIG. 2 shows the protective cover 3 inserted over the opening 9 of the protective cap to therefore seal the interior 8 from contamination. More particularly, the cover 3 is of substantially cylindrical section having an inner diameter corresponding substantially to the outer diameter of the cover above the flange at 5 so that a tight frictional fit can be afforded. A topmost portion of the cover remote from the flange includes a necked down area 6 have a plurality of faces on an outer wall thereof to provide tactile means in combination with the longitudinally extending ribs 7 for purposes to be assigned. The faces on the end of the cover 6 analogously operate as the exterior faces on a nut.

In use and operation, a syringe S having a needle N is adapted to be placed within the cover 10, and an area of the cover away from the opening 9 is grasped with mechanical advantage being afforded by the longitudinally extending ribs 7. Misalignment of the syringe needle N with respect to the opening 9 can be accounted for (absent gross alignment) and guarded against by means of the radially extending flange 2. The inner diameter of the interior 8 is engineered and designed to accommodate the outer periphery of the needle support base such that rotation of the syringe S will cause dislodgement of the needle N from the syringe whereby the syringe is ready to receive a new needle thereon.

New needles can be removed and old needles can be replaced within the cap for the associated security and hygienic aspects to which the instant invention is directed. The cover 3 can be twisted from the protective cap body, be means of the mechanical advantage on the multifaceted end portion 6 vis a vis the longitudinally extending ribs 7.

FIGS. 4, 5 and 6 depict the protective cap placed in a special storage receptacle packaged so that a plurality of such caps can be sold and transported in quantity.

More particularly, the special receptable 20 includes a container having a bottom wall 22, from which upwardly extends four side walls 21. Thus, an open top container is provided. A flap 24 extending from one edge of one of the side walls 21 is adapted to rotate on top of the open top and therefore occlude the open top and a flap lip 25 is provided for closing. The interior of the special receptacle includes a shelf 23 provided with a plurality of holes 26 which allows the protective caps 10 to be disposed in a pattern by protruding longitudinally through the holes 26 supported by the flanges 2. That is to say, four caps 10 are disposed to form a substantially square cluster with sufficient clearance for a fifth cap 10 to be disposed in the center area between the four other caps. The four caps are sufficiently close to each other so that when a fifth central cap is placed as shown in FIG. 6, a nesting occurs for economy of space. Thus a matrix is defined formed from a plurality of clusters, each cluster having N caps circumscribing a central cap and spaced from each other so that the radius of the flange 2 of the central cap has adequate clearance for overlying disposition on the peripheral group of caps. As should be evident from FIG. 5, a plurality of such clusters can be formed so that one marginal edge of the one cluster is a member of an adjacent cluster. In the specific example of FIG. 5, the cluster is formed from four peripherally disposed caps and on central cap. It should be apparent that those caps which are placed in the center of a cluster form clusters of their own with three immediately adjacent central caps so that clusters, when arranged as shown in FIG. 5, define another cluster formed exclusively of overlying caps disposed in the centers of the underlying clusters. As shown in FIG. 5 therefore, an underlying array of three rows and three columns of caps will define a central cluster upon which four overlying caps are adapted to be disposed. Thus when a cluster formed from an N×N array is arranged to form a matrix having N rows and columns, a second superposed cluster is available to be disposed upon the underlying matrix.

Having thus described the invention it should be apparent that numerous structural modifications are contemplated as being part of this invention as set forth herein above and as defined herein below the claims.

I claim:

1. A protective device for receiving and storing a hypodermic needle therein, the needle having an upper portion formed with an annular lip, comprising: a substantially tubular housing having a cylindrical side wall, an end wall forming a first closed end, and a second opposite open end for slidably receiving the hypodermic needle with a relatively snug fit therebetween, such that the end of the needle is spaced from the closed end of the tubular housing, and such that the lip on the upper portion of the needle is spaced axially from the open end of the tubular housing, thereby facilitating sliding removal of the needle from the tubular housing, an annular flange formed integrally on the cylindrical side wall in a position substantially closer to the second open end than to the first closed end, whereby the cylindrical side wall of the tubular housing has an upper minor portion above the annular flange and a lower major portion below the annular flange; a substantially cylindrical cover having a top portion and further having a bottom open end formed therein, wherein the cover may be slidably received over the upper minor portion of the cylindrical side wall of the tubular housing with a relatively snug fit therebetween, and wherein the bottom open end of the cover abuts against the annular flange on the cylindrical side wall of the housing.

2. The device of claim 1, wherein the housing being further comprised of a plurality of longitudinally extending ribs being positioned on the lower portion of the cylindrical wall.

3. The device of claim 1, wherein the cover is further provided with tactile means for grasping said cover to aid in the placement and removal thereof.

4. A protective device for receiving and storing a hypodermic needle therein, the needle having an upper portion formed with an annular lip, comprising: a substantially tubular housing having a cylindrical side wall, an end wall forming a first closed end, and a second opposite open end for slidably receiving the hypodermic needle with a relatively snug fit therebetween, such that the end of the needle is spaced from the closed end of the tubular housing, and such that the lip on the upper portion of the needle is spaced axially from the open end of the tubular housing, thereby facilitating sliding removal of the needle from the tubular housing, an annular flange formed integrally on the cylindrical side wall in a position substantially closer to the second open end then to the first closed end, whereby the cylindrical side wall of the tubular housing has an upper minor portion above the annular flange and a lower major portion below the annular flange; a substantially cylindrical cover having a top portion and further having a bottom open end formed therein, wherein the cover may be slidably received over the upper minor portion of the cylindrical side wall of the tubular housing with a relatively snug fit therebetween, and wherein the bottom open end of the cover abuts against the annular flange on the cylindrical side wall of the housing, wherein the housing being further comprised of a purality of longitudinally extending ribs being positioned on the lower portion of the cylindrical wall, and further wherein the cover is further provided with tactile means for grasping said cover to aid in the placement and removal thereof.

* * * * *